(12) United States Patent
Gill et al.

(10) Patent No.: US 6,502,452 B1
(45) Date of Patent: Jan. 7, 2003

(54) METHOD OF TESTING BOILER TUBE INTEGRITY AND PROBE FOR SAME

(75) Inventors: Chad Evans Gill, Lynchburg, VA (US); Mark Alan Klahn, Forest, VA (US)

(73) Assignee: Framatome ANP, Inc., Lynchburg, VA (US)

( * ) Notice: Subject to any disclaimer, the term of this patent is extended or adjusted under 35 U.S.C. 154(b) by 0 days.

(21) Appl. No.: 09/650,925

(22) Filed: Aug. 29, 2000

(51) Int. Cl.[7] .......................... G01M 3/04; F16L 55/10; G01N 27/72
(52) U.S. Cl. .......................... 73/49.8; 73/49.5; 138/90; 324/220
(58) Field of Search .................. 138/89–91; 73/49.8, 73/49.5, 49.6; 324/220

(56) References Cited

U.S. PATENT DOCUMENTS

| | | | | |
|---|---|---|---|---|
| 188,625 A | * | 3/1877 | Hand | 138/89 |
| 1,587,663 A | * | 6/1926 | Lundgren | 138/91 |
| 2,581,536 A | * | 1/1952 | Johns | 138/90 |
| 5,797,431 A | * | 8/1998 | Adams | 138/89 |
| 6,035,898 A | * | 3/2000 | Dominguez | 138/89 |
| 6,170,530 B1 | * | 1/2001 | Steblina | 138/89 |

* cited by examiner

Primary Examiner—Hezron Williams
Assistant Examiner—Michael Cygan
(74) Attorney, Agent, or Firm—Vytas R. Matas

(57) ABSTRACT

A tube testing system consists of two subassemblies, the probe and the applicator. The probe uses a stack of Belleville style washers that when compressed allow the locking fingers to relax and the probe to be inserted into the tube. Once the probe is placed in the correct location using the applicator, the Belleville style washers are allowed to expand, locking in the fingers and engaging the urethane seals. As the water fills the tube, the air is pushed through a bleed hole in the mandrel of the probe. The bleed hole leads to a chamber in the top of the probe that contains a plastic ball. The ball floats on water and as the chamber fills, the ball seals off the leak path and the tube can then be pressurized and the test performed. Once the test is complete, the water is drained and using the applicator, the probe is removed from the tube.

8 Claims, 3 Drawing Sheets

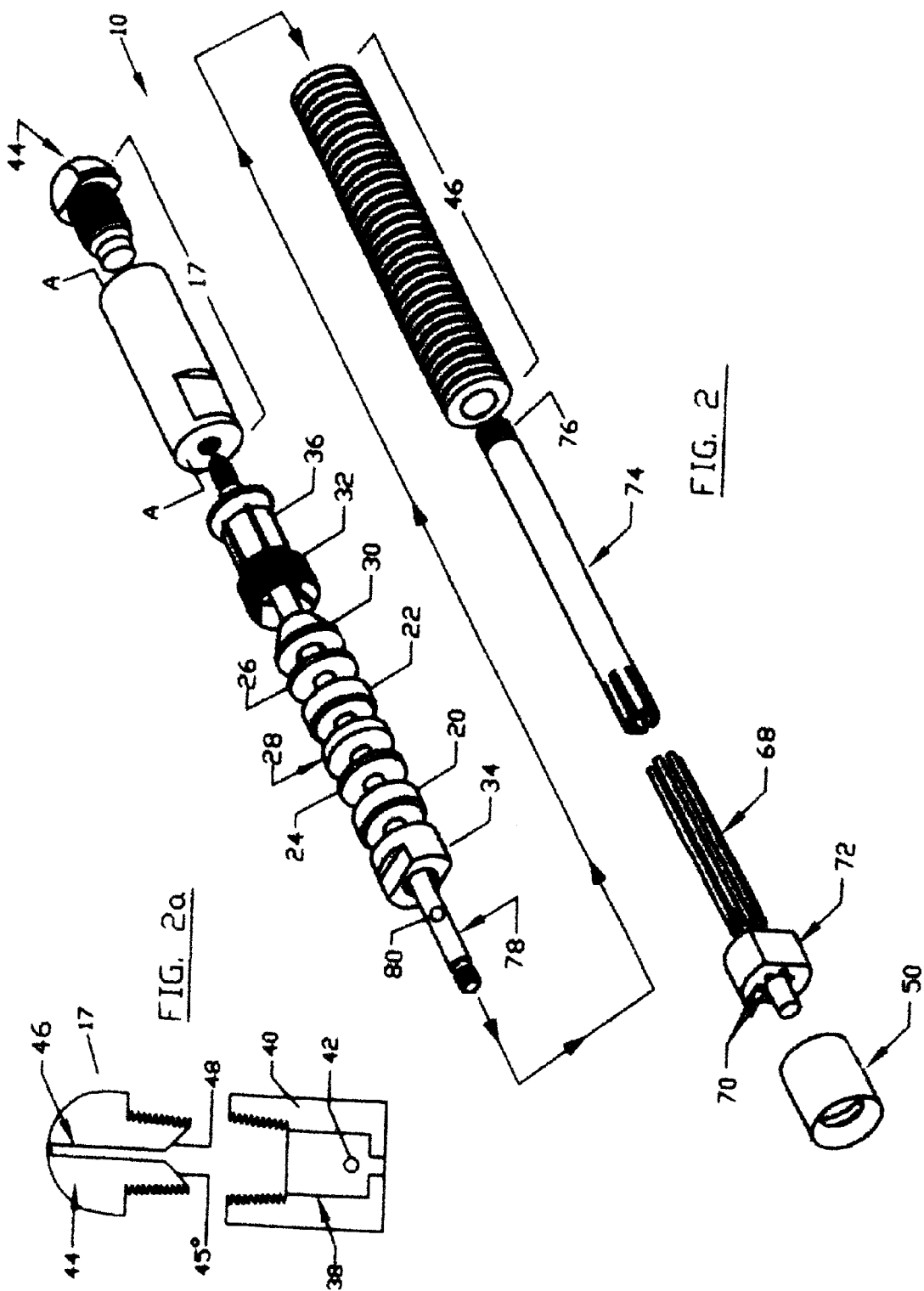

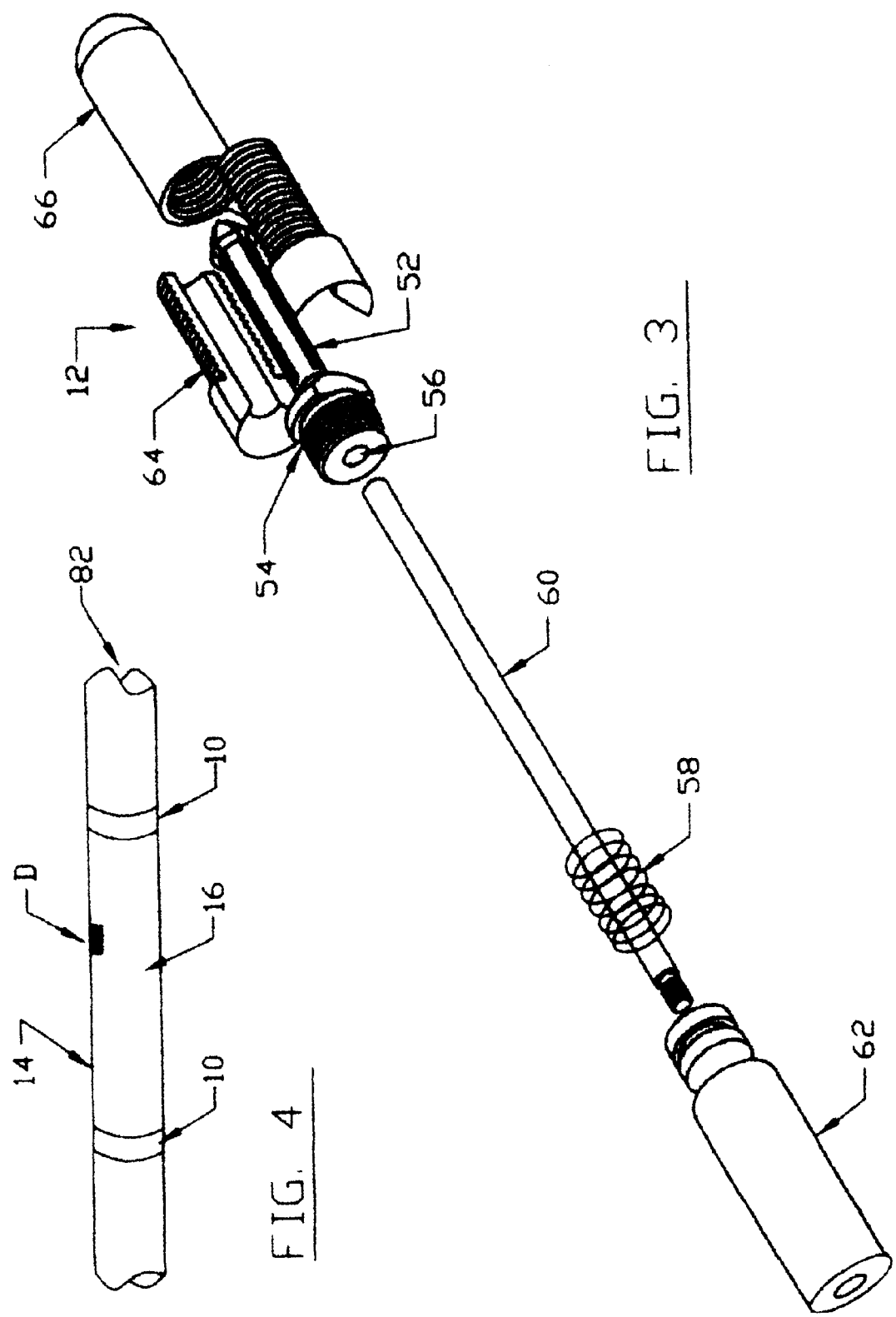

METHOD OF TESTING BOILER TUBE INTEGRITY AND PROBE FOR SAME

BACKGROUND OF THE INVENTION

1. Field of the Invention

The present invention is generally drawn a method of testing the integrity of boiler tubes and more particularly for localized testing of same with a unique test probe.

2. Description of the Prior Art

Testing boiler tubes for defects is known in the art and various methods and apparatus are employed.

Eddy current meters are passed through tubing and defects such as cracks in the tubing and thin wall sections are detected thereby. U.S. Pat. No. 5,025,215 teaches the use of such eddy current meters to detect defects in steam boiler tubes.

It is also known to plug steam tubing with a plug having grasping fingers and urethane seals and then to subject it to a high pressure to determine if there is any leakage therefrom. Such a method and plug are disclosed in U.S. Pat. No. 4,385,643.

However, toate there was no teaching in the prior art of localizing a particular area of the steam tubing which may have a potential tube problem and then sealing only this localized section and subjecting it to pressures in excess of normal operating pressures to determine if this defect is one that will fail in service.

SUMMARY OF THE INVENTION

The present invention solves the problems associated with prior art devices and others by providing a unique steam tube testing method and apparatus for same whereby tubes are checked for potentially defective areas which may fail in the future by leaking and to a special probe used for isolating and high pressure testing these areas.

The method involves first testing the boiler tube for defective areas using an electromagnetic probe. Once the defective area is thus identified and localized, a probe is inserted about 3" past the defect using a probe applicator. The probe is then sealed to the inside of the tube and the applicator is removed. A second probe is similarly located on the other side of the defect. The tube section between the two probes is then filled with water to evacuate all air there from that may cause a bad reading and the tube is fluid pressurized to approximately 3× the normal steam tubing operating pressure to see if the defect is truly a defect which may result in a leak. If a leakage results, the tube is later sealed in a known manner. If there is no leak, the tube is deemed operationally fit. The probes are then removed and another area is similarly checked.

The probe assembly comprises the probe and the applicator for driving the probe to the desired location. The probe uses a stack of Belleville style washers that are compressed to relax a series of locking fingers allowing the probe to be moved to the location by the applicator. Once there, the washers are expanded to lock the fingers to the tube and to expand urethane seals to seal the tube. The applicator is then removed and a water supply probe is inserted in the tube creating the localized chamber.

In view of the foregoing it will be seen that one aspect of the present invention is to provide a method and apparatus for checking a localized section of steam tubing for potential future failure.

Another aspect is to provide an easily inserted and retracted apparatus for sealing a section of steam tubing.

Yet another aspect is to provide a method and apparatus for testing the integrity of steam tubing exclusively from the inside of the tubing allowing for simultaneous testing of the tubing outside surface.

These and other aspects of the present invention will be more fully understood upon a review of the following description of the preferred embodiment when considered in conjunction with the drawings.

BRIEF DESCRIPTION OF THE DRAWINGS

In the drawings:

FIG. 2 is a schematic representation of the disassembled probe assembly used in the FIG. 1 testing method;

FIG. 2a is an expanded cross-sectional view of the top of FIG. 2 taken along section A—A;

FIG. 3 is a schematic representation of the disassembled applicator assembly used to drive the probe to a desired location; and FIG. 4 shows a section of steam tubing having a localized section of steam tubing sealed for testing.

DESCRIPTION OF THE PREFERRED EMBODIMENT

Figure 1:
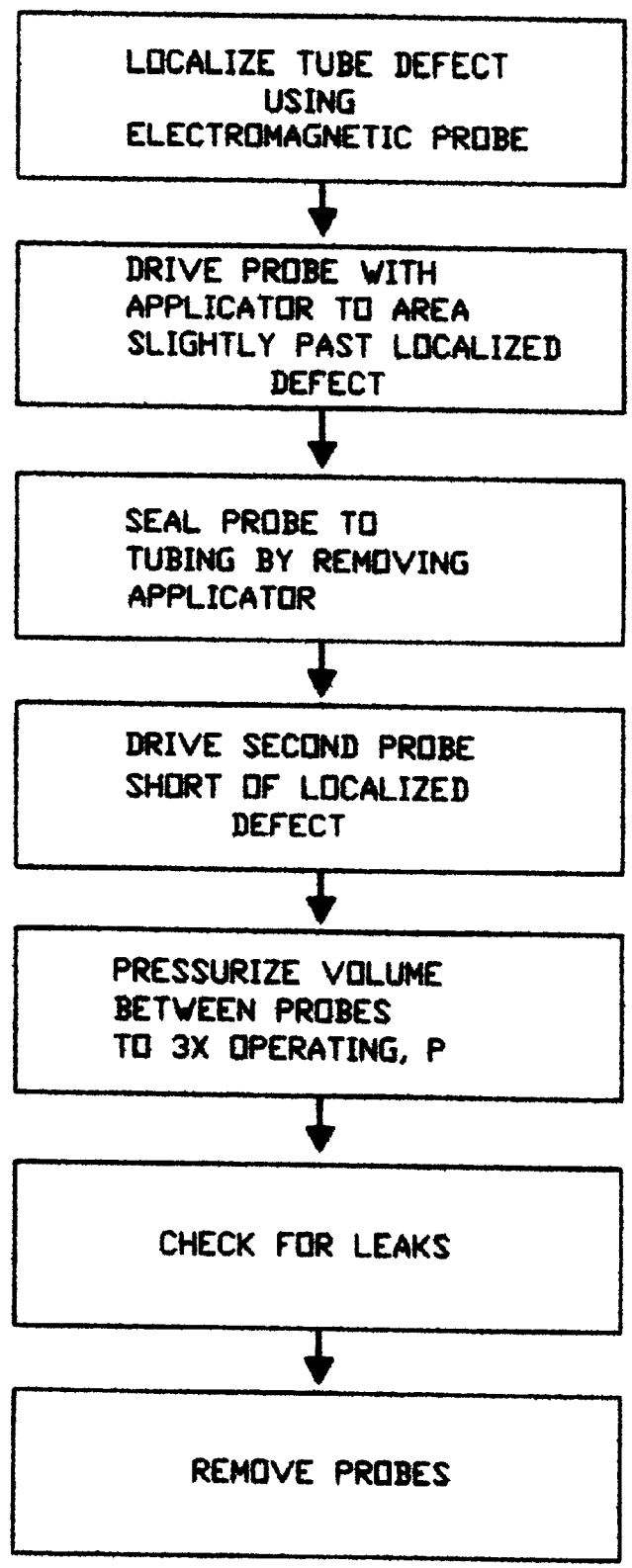
FIG. 1 is a flow chart of the tube testing method of the present invention.

Referring now to the drawings, the In-Situ pressure testing system of the present invention is used for the hydro testing of heat exchanger tubing in nuclear steam generators. The system uses known test devices such as a pump, data acquisition system and flow delivery probes in various arrangements for testing (not shown).

The purpose of the In-Situ Pressure testing system is to perform In-Situ testing of steam generator tubing while using only a single channel head. The complete system includes the probe assembly (10) and an applicator assembly (12) used for installation and retrieval of the probe assembly (10). In order to create a test chamber the two ends of a section of steam tubing (14) must be sealed and water supplied to the sealed chamber (16). The probe (10) acts as one sealed end of the chamber. A second, unattached probe (10') is added to the tube to create the second seal as well as deliver the water and pressurize the chamber (16).

The probe (10) is untethered and self locking, bleeding and sealing during the testing process from a bleed assembly (17). It is these four characteristics that make this probe (10) effective and unique in its application. The probe (10) uses 31 pairs of Belleville style washers (18). These washers (18) supply the force and stroke which locks the probe into the tubing (14) both securing and sealing the end of the created test chamber (16). The applicator (12) hydraulically compresses the washers (18) making it possible for the probe (10) to be fully locked in the tube (14). The probe has two seals (20,22) and back-up washers (24,26) a washer (28) wedge (30) and collet (32), which are added beneath the bleed assembly (17). Once tightened to secure all connections, the probe is installed into the tubing (14). The applicator (12) is then removed from the tube leaving the probe (10) unconnected.

The expansion of the washers accomplishes two functions at once. As the washers (18) expand, the distance between the bleed assembly (17) and the top holder (34) is decreased. This in turn forces the wedge (30) into the collet (32) spreading fingers (36) which react on the tube (14) wall thus locking the probe (10) in place. This also squeezes the seals (20,22) between the other components causing them to expand creating a watertight seal.

Since it is necessary to bleed the air from the test chamber (16) in order perform an effective test, a check valve is placed in the top of the probe (10). A passage (38) is drilled through the mandrel (40) connecting the bleed assembly (17) to the test chamber. The bleed assembly (17) houses a check valve including a polyethylene ball (42) and a tapered top or plug (44). As water forces the air from the chamber, it comes to the bleed assembly (17) flowing around the ball (42) and out of the through hole (46) in the plug (44). Once all of the air has been evacuated, water follows the same path. The ball (42) however, floats on water and is then forced against the taper (48) in the bottom of the plug (44). The ball (42) seals off the flow path and the probe and the chamber beneath it is now bled, sealed and ready for testing.

Once the test is complete the lower water supplying toolhead is removed and the water pressure released. The ball (42) releases from the taper as the water level drops and the check valve is now reset. All that now remains is to retrieve the probe. The applicator (12) is inserted back into the tube until it fits in a bottom receiver (50) of the probe. Both the receiver and the fingers are tapered to ensure proper alignment and function. The hydraulic cylinder is actuated and the push rod extends. The push rod spreads the fingers apart securing the applicator to the probe. The rod continues forward striking the connect washer. The washer, which slides along six rods, transfers the force to the stack of washers compressing them and relaxing the finger and seal arrangement above. Once fully actuated, the probe (10) is pulled by the applicator (12) and removed from the tube.

Turning to FIG. 3 it will be seen that the applicator (12) comprises a series of expanding fingers (52) connected to a threaded bowl (54) having an aperture (56) extending through a threaded base (54) and fingers (52). A spring (58) is wound around a piston rod (60) which is screwed into a known hydraulic or air piston drive (not shown) located inside housing (62). The base (54) is also threaded into the housing (62) and allows the piston rod to move in the aperture (56) to spread the fingers (52) and capture the receiver end (50) of the plug (10) when inserting or removing the plug (10). A threaded protective sheath (64) is mounted partially over the fingers (52) and is able to receive a threaded protective cap (66) when the applicator (12) is not in use.

Turning next to FIG. 2 it will be seen that the receiver (50) is connected to the probe (10) through a series of circumferential rods (68), which slidably extend through holes (70) in sliding member (72), which slides along the rods (68), to be threaded into the receiver (50). The other ends of the rods (68) are retained in a rod holder (74). The Belleville washer array (18) slides along this rod holder (74) and the rods (68) in response to movement of the slide member (92) along the rods (68). The threaded end (76) of the rod holder (74) is threaded into the retaining member (34) through whom a hollow shaft (78) extends to be screwed into the bleed assembly (17) at one end and into the slide (72) at the other end. A hole (80) at one end of the shaft (78) provides fluid communication to the bleed assembly (17) through the threaded connection at the other end of the hollow shaft (78). The urethane seals, washers, collet and fingers are slidably mounted on the hollow shaft (78).

Next looking at all the Figures, it will be seen that in performing the test, the pipe (14) is first tested in a known manner with a known electromagnetic probe (not shown) to determine the area where a potential defect D is present. The applicator (12) is then attached to the plug (10) through fingers (52) in receiver (50). The piston (60) drives the sliding member (72) along the rails (68) to shorten the space within which the Bellville washers (18) are located thus compressing the washers to allow them to slide along the inside diameter of the pipe (14). The same movement of the member (72) allows more space along shaft (78) for the urethane seals (20, 22) and the fingers (36) thus diminishing their diameters so as to allow them to fit inside pipe (14). The plug (10) is then driven from an inlet (82) of the pipe to a location approximately 3" past the defect D. The applicator is removed and the spaces between washers (18) and fingers (36) and seals (20, 22) restored. The 31 pairs of Bellville washers provide the needed force to expand the seals (20,22) and fingers (36) to set the plug (10) in the tube. A second plug (10') identical to plug (10) is driven in a similar manner just short of the defect D creating the sealed space (16). The receiver (50') of the plug (10') applies a water source, which evacuates the air from the space (16) and pressurizes it to 3× normal operating pressure in a manner described earlier. The defect D is then checked for leaks and if a leak develops, is plugged or lined in a known manner after the plugs (10) and (10') are removed by the applicator in the same manner described as to their insertion.

From the foregoing it will be seen that there are three main advantages of this probe over previous tooling. First is the single channel head access. Prior to this the only way to perform a localized test while maintaining the axial load was to use a probe inserted from the opposite channel head. This process stopped operation in both sides for testing in just one. Secondly, there are no corrections for the chamber pressure and loads created due to tooling in the chamber taking up area and carrying a portion of the loads. The two probes that create the chamber are independent of each other and free to move relative to each other. The pressure-induced loads are carried solely by the tube itself and most closely model the true situation. Lastly, there are infinite arrays of chamber lengths that can be created with this probe as part of the chamber. The only single channel probes are unable to encompass a wide variety of lengths from inches to the entire length of straight tubing. It is these three main advantages that set this probe apart from all others affiliated with this type of testing.

Certain modifications and additions will occur to those skilled in the art area upon reading this disclosure. As an example, alternatives to the probe arrangement include the substitution of springs or other force suppliers for the Belleville style washers. The hydraulics involved could also be substituted with air cylinders or lead screws. Also, for OTSG specific applications a probe of this nature could be used without the bleed assembly and the water supplied from above the probe. Different sizes may be created for application in tubes of various sizes. It will be understood that all such were deleted herein for the sake of conciseness and readability but are intended to fall within the scope of the following claims.

What is claimed is:

1. A tube testing assembly for sealing a section of tubing comprising;

a probe assembly having expanded sealing means for sealing a section of tubing in a first position and having contracted sealing means in a second position allowing free movement within the tubing; and an applicator assembly connectable to said probe assembly to place said sealing means in the second position when connected thereto to locate the probe in the tubing and disconnectable from said probe assembly to place said sealing means in the said first position thereby to seal the tubing; and said probe assembly including a series of Bellville washers and a seal assembly wherein said series of Bellville washers is contracted and said seal assembly is relaxed in said second position and said series of Bellville washers is released to expand said seal assembly in said first position.

2. A tube testing assembly as set forth in claim 1 wherein said seal assembly includes at least a pair of urethane seals.

3. A tube testing assembly as set forth in claim 2 including a pair of washers separating said urethane seals.

4. A tube testing assembly as set forth in claim 1 wherein said seal assembly includes a series of circumferential fingers expandable to contact and inside wall of the tubing in said first position and contracted to have a diameter smaller than said inside tubing in said second position.

5. A tube testing assembly as set forth in claim 3 wherein said applicator assembly includes a piston shaft movable to compress said series of Belleville washers and relax said pair of urethane seals in an extended position when connected to said probe assembly.

6. A tube testing assembly as set forth in claim 5 wherein said probe assembly includes a bleeder assembly connected to one end of said probe assembly for exhausting air therethrough.

7. A tube testing assembly as set forth in claim 6 wherein said bleeder assembly includes a check valve for sealing said bleeder assembly when water is passed therethrough.

8. A tube testing assembly as set forth in claim 2 wherein said check valve includes a floating ball for sealing a V-shaped groove having an exhaust aperture therein when said check valve is subjected to water.

\* \* \* \* \*